(12) United States Patent
Engel et al.

(10) Patent No.: US 6,319,192 B1
(45) Date of Patent: Nov. 20, 2001

(54) METHOD FOR THE TREATMENT OF FERTILITY DISORDERS

(75) Inventors: Jürgen Engel, Alzenau; Hilde Riethmüller-Winzen; Thomas Reissmann, both of Frankfurt, all of (DE)

(73) Assignee: Zentaris AG, Frankfurt am Main (DE)

( * ) Notice: Subject to any disclaimer, the term of this patent is extended or adjusted under 35 U.S.C. 154(b) by 0 days.

(21) Appl. No.: 09/296,610

(22) Filed: Apr. 23, 1999

Related U.S. Application Data

(60) Provisional application No. 60/082,743, filed on Apr. 23, 1998.

(51) Int. Cl.$^7$ .................................................. A61B 17/43
(52) U.S. Cl. ............................................................. 600/33
(58) Field of Search ................................... 600/33–35

(56) References Cited

U.S. PATENT DOCUMENTS

| 5,130,137 | 7/1992 | Crowley, Jr. | |
| 5,824,548 | * 10/1998 | Hearn | 600/33 X |
| 6,004,260 | * 12/1999 | Thompson | 600/33 |
| 6,022,860 | * 2/2000 | Engel et al. | 514/15 |

FOREIGN PATENT DOCUMENTS

| 2115943 | 8/1994 | (CA) . |
| 196 04231 A1 | 7/1997 | (DE) . |
| 0 788 799 | 8/1997 | (EP) . |

OTHER PUBLICATIONS

Bouchard P. et al., "Endocrine features of combined gonadotropin and GNRH antagonist ovulation induction" OVUL. IND. Update '98, Proc. World Conf., 2nd, 1998, 1997, Seiten 115–119, XP002111491.

* cited by examiner

Primary Examiner—John P. Lacyk
Assistant Examiner—Joseph A Cadugan
(74) Attorney, Agent, or Firm—Pillsbury Winthrop LLP

(57) ABSTRACT

An improvement to the method of intrauterine insemination by the administration of luteinizing hormone-releasing hormone antagonists (LHRH antagonists).

6 Claims, No Drawings

METHOD FOR THE TREATMENT OF FERTILITY DISORDERS

This application claims benefit of provisional No. 60/082,743 filed Apr. 23, 1998.

BACKGROUND OF THE INVENTION

1. Field of the Invention

The invention relates to the use of luteinizing hormone-releasing hormone antagonists (LHRH antagonists) in intrauterine insemination.

2. Background Information

One of the ethical problems of more recent times is the increasing sterility and unwanted childlessness of many couples. With respect to the therapy of these fertility disorders, inter alia, the following treatment methods of artificial fertilization have been established:

1. Substitution therapy—applied in patients with hypogonadotropic amenorrhoea
2. Stimulation therapy—given to anovulatory patients with active, albeit deranged hypothalamic pituitary-ovarian axis
3. Regulation therapy—employed in women with polycystic ovary disease (PCOD)
4. Hyperstimulation therapy—used in in vitro fertilization (IVF), gamete intrafallopian transfer (GIFT), tubal embryo transfer (TET), intracytoplasmatic sperm injection (ICSI) and intrauterine insemination (IUI).

The present invention especially relates to the improvement of the method of artificial sperm cell transfar in the uterus, i.e. the ferrtilization by intrauterine insemination (IUI) mentioned under item 4.

For the methods under items 2 and 4, it is necessary to stimulate follicle growth, which is achieved by the administration of gonadotropins, e.g. human menopausal gonadotropin (HMG or hMG), follicle stimulating hormone (FSH), and luteinizing hormone (LH), with or without preliminary therapy with clomiphene. It has further proved that the risk of luteinization by a premature LH surge, which leads to unfavourable implantation conditions arid relatively low pregnancy rates, can be decreased by complete suppression of the endogenous gonadotropins using gonadotropin releasing hormone (GnRH) agonists (Garcia et al. , 1984; Navot et al. , 1991; Hoffmann e al. , 1993).

For the control of ovarian stimulation with subsequent induction of ovulation, with the aim of obtaining fertilizable egg cells, both recombinant FSH and HMG and FSH and HMG obtained from urine are employed.

In connection with IUI, it is also desirable to control follicle growth and to specifically trigger ovulation.

The statements in the specialist literature about the therapeutic accompaniment of IUI, in particular using GnRH analogues, are mainly negative, such as, for example, the following:

1. IUI after ovarian stimulation with clomiphene may be important as the $1^{st}$ choice of therapy, provided the male partner has a normal spermiogram (Hum. Reprod. 1997; July; 12(7):1458–1463).
2. GnRH agonists/HMG stimulation, however, may be ineffective in routine IUI. Treatment with GnRH agonists with maximum suppression of the endogenous gonadotropins requires a relatively long treatment period (about 3 weeks) and leads to an increased consumption of HMG and is associated with side effects.
3. Reports also exist which confirm that an increase in the pregnancy rate is not achieved by the use of GnRH agonists/HMG against HMG alone for IUI treatment in the case of unclarified infertility (Hum. Reprod. 1994 June 9(6)1043–1047.
4. The cost differences of GnRH-a/HMG stimulation compared with clomiphene/HMG is indicated by Finnish authors an Eur. J. Obstet. Gynecol. Reprod. Biol. 1997 July 74: GnRH-a/HMG stimulation is not cost-effective in routine IUI therapy.

In a study by Diedrich et al. from 1994 Hum. Reprod. 1994 May; 9(5), the suppression of the undesired, premature LH surge by cetrorelix during ovarian stimulation with HMG and the on-time induction of ovulation was described in the context of a COS-ART study.

It was possible to shorten the length of the treatment period using this LHRH antagonist and the partial dose-dependent suppression of the endogenous gonadotropins additionally proved advantageous, since it was possible to reduce the consumption in comparison to the use of agonists of HMG.

DESCRIPTION OF THE INVENTION

The object of the invention is therefore to improve, i.e. to make inexpensive and more effective, the treatment method of intrauterine insemination known per se and thus in the end to fulfill the desire for children of many couples.

It has now been found that the treatment method of IUI can be improved by carrying out a partial suppression of the endogenous gonadotropins, which can only be achieved by means of LHRH antagonists, preferably cetrorelix or antarelix. At the same time, follicle growth is stimulated by means of urinary or recombinant FSH, HMG or clomiphene, or a combination thereof. Subsequently, ovulation can be triggered at a desired time by means of human chorionic gonadotropin, native LHRH, LHRH agonists or recombinant LH. Surprisingly, this takes place when the dominant follicle has reached a diameter of about 16–18 mm. Intrauterine sperm injection then takes place with the aim of intracorporeal fertilization. It is possible in this way to carry out a stimulation treatment which is less stressful for the patient and guarantees a high degree of safety with respect to the ovulation time and leads to a saving in cost.

What is claimed is:

1. In the method of therapeutic management of infertility by intrauterine insemination, the improvement consisting of
   a) the dose-dependent suppression of endogenous gonadotropins, especially LH, with an LH-RH antagonist allowing the maintenance of physiological oestrogen levels
   b) exogenous stimulation of the ovarian follicle growth
   c) ovulation induction with HCG, native LHRH, LHRH agonists or recombinant LH
   d) intrauterine insemination by sperm injection.
2. The method of therapeutic management of infertility by intrauterine insemination according to claim 1 in which the LHRH antagonist is cetrorelix.
3. The method of therapeutic management of infertility by intrauterine insemination according to claim 1 in which he LHRH antagonist is antarelix.
4. The method of therapeutic management of infertility by intrauterine insemination according to claim 1 in which ovarian follicle stimulation is performed by administration of urinary or recombinant FSH or HMG, with or without recombinant LH.

5. The method of therapeutic management of infertility by intrauterine insemination according to claim 1 in which ovarian follicle stimulation is achieved with antioestrogens.

6. The method of therapeutic management of infertility by intrauterine insemination according to claim 1 in which ovarian follicle stimulation is achieved with the combination of antioestrogens with gonadotropins.

* * * * *